United States Patent [19]

Seipenbusch

[11] Patent Number: 4,874,700
[45] Date of Patent: Oct. 17, 1989

[54] PROCESS FOR THE PRODUCTION OF L-MALIC ACID

[75] Inventor: Reinhold Seipenbusch, Gladbeck, Fed. Rep. of Germany

[73] Assignee: Huels Aktiengesellschaft, Marl, Fed. Rep. of Germany

[21] Appl. No.: 778,464

[22] Filed: Sep. 20, 1985

[30] Foreign Application Priority Data

Sep. 22, 1984 [DE] Fed. Rep. of Germany ....... 3434918

[51] Int. Cl.$^4$ .............................................. C12P 7/46
[52] U.S. Cl. .................................. 435/145; 204/182.3; 435/136; 562/580; 562/582; 562/593; 562/595
[58] Field of Search .............................. 435/136, 145; 204/182.3, 182.4, 182.5, 182.6, 301; 562/580, 582, 593, 595

[56] References Cited

U.S. PATENT DOCUMENTS

| | | | |
|---|---|---|---|
| 3,371,112 | 2/1968 | Winstrom et al. | 562/580 |
| 3,391,187 | 7/1968 | Cullen, Jr. et al. | 562/580 |
| 3,873,425 | 3/1975 | Kobayashi et al. | 435/145 |
| 3,922,195 | 11/1975 | Chibata et al. | 435/145 |
| 3,964,985 | 6/1976 | Giuffrida | 204/182.6 |
| 4,486,283 | 12/1984 | Tejeda | 204/182.4 |

OTHER PUBLICATIONS

*Desalination*, 10 (1972) 157–180.

*Primary Examiner*—Barry S. Richman
*Assistant Examiner*—Timothy M. McMahon
*Attorney, Agent, or Firm*—Millen, White & Zelano

[57] ABSTRACT

L-malic acid is separated by means of electrodialysis from reaction mixtures derived from biotechnical conversion of fumarate into L-malate. Fumaric acid present in the acid concentrate from the dialysis is separated from L-malic acid without precipitation reactions using stepwise crystallization. Crystallized L-malic acid is produced in high purity and large yield. The alkali concentrate obtained during electrodialysis is recycled back into the biotechnical conversion. The process operates without appreciable losses of valuable materials and is very economical.

17 Claims, 2 Drawing Sheets

PROCESS FOR THE PRODUCTION OF L-MALIC ACID

BACKGROUND OF THE INVENTION

The present invention relates to a process for the production of L-malic acid (LMA) by biotechnical conversion of fumaric acid. During this process, a reaction mixture is obtained containing, besides the desired LMA, unreacted fumaric acid and other nonionic compounds from the biotechnical conversion. LMA and fumaric acid are normally present in the form of salts.

The biotechnical conversion of fumaric acid into LMA is known and is carried out by means of various processes. It is possible to use bacteria (DAS 2,363,285), immobilized bacteria (Europ. J. Appl. Microbiol. 3 . 169-183 [1976]; U.S. Pat. No. 3,922,195), fungi (DOS 3,310,849), immobilized fungi (DOS 2,450,137), or the enzyme fumarase isolated from microorganisms (DAS 2,415,310). The LMA salt can be present in the reaction mixture in a moderately high concentration or in a high concentration (DOS 3,310,849; U.S. Pat. No. 592,977 of Mar. 23, 1984 and DOS 3,434,880; U.S. 654,070 of Sept. 24, 1984). Furthermore, the biotechnical conversion of glucose into LMA has been described by a symbiosis between a fungus and a bacterium (J. Ferment. Technol. 54 : 197-204 [1976]).

Various processes have been known for the separation of LMA from the reaction mixture. For example, a large amount of a calcium compound can be added to the fermentation batch whereby the thus-formed LMA precipitates as the calcium malate as early as during the fermentation (DOS 1,417,033). The reaction mixture can also be treated with cation exchangers; the eluates, after concentration, are filtered and evaporated (DOS 3,247,981). Furthermore, it is possible to separate, by acidification, the unreacted fumaric acid from the mixture and thereafter precipitate the LMA as the calcium salt. This salt can be reacted with sulfuric acid to form calcium sulfate and LMA, the latter being treated with an ion exchanger to remove the dissolved calcium sulfate.

The conventional processes for obtaining LMA by biotechnical conversion of fumaric acid have the following characteristics, inter alia:

Upon acidification of the reaction mixture for the purpose of separating the unreacted fumaric acid, a salt is formed from the added acid and the cations contained in the reaction mixture; this salt, after the subsequent calcium precipitation of the LMA, though remaining in the filtrate for the largest part, is also found to a certain extent in the filter cake of Ca malate.

The filter cake must be washed salt-free and clean. During this step, losses of Ca malate occur whereby the LMA yield is reduced. The filtrate and the washing water are discarded.

The alkaline solution added prior to the biotechnical conversion for neutralizing the fumaric acid is practically unrecoverable, and thus is entirely lost after a one-time use.

During reaction of Ca malate with sulfuric acid, Ca sulfate (gypsum) is obtained as an unavoidable by-product. The removal of this product burdens the process with additional expenses.

It is frequently difficult to obtain the LMA in the desired high purity with a simultaneously high yield.

A problem, therefore, exists in improving separation of LMA from the reaction mixture so that LMA can be obtained in high purity with a large yield, under economical conditions.

SUMMARY OF THE INVENTION

Accordingly, it is an object of this invention to provide a solution to this problem and render separation of LMA from the reaction mixture more economical.

It is a further object of this invention to enable the LMA to be obtained in maximally pure form, and, preferably, to enable recovery of other compounds contained in the reaction mixture in a reusable form, e.g., in a form suitable for recycling.

Upon further study of the specification and appended claims, further objects and advantages of this invention will become apparent to those skilled in the art.

These objects have been attained by this invention by providing a process for obtaining LMA from reaction mixtures formed during the biotechnical conversion of fumaric acid salts into LMA salts, the mixtures being practically free of cellular substances or having previously been freed conventionally thereof, and this process comprising:

continuously separating the reaction mixture in a
      conventional electrodialysis unit (EDU) having at
      least three cells into
      the acid concentrate, containing LMA and fumaric
         acid,
      the alkali concentrate,
      the diluted product, containing the nonionic components of the reaction mixture, the remainder of fumarate and L-malate, and any other salts,
   working up the acid concentrate to obtain pure LMA
      according to conventional processes, and
   collecting the alkali concentrate for reuse.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION

Figure 1:
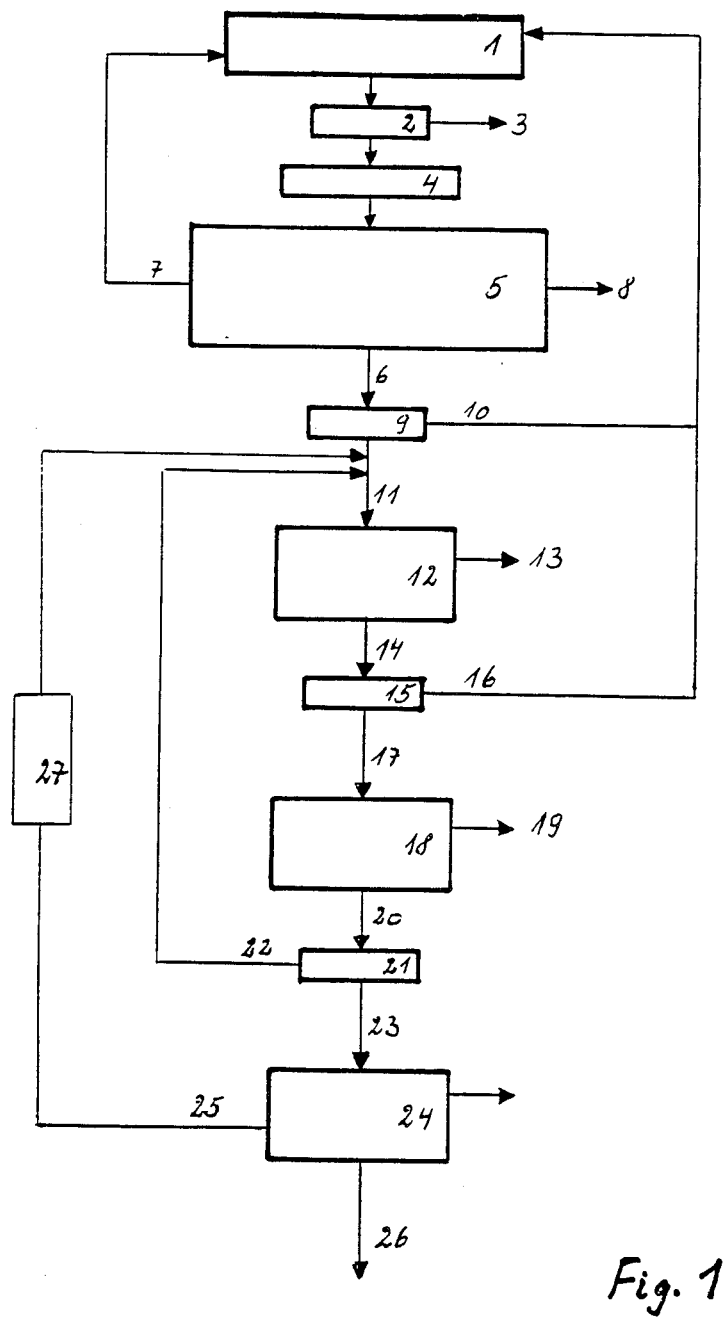
FIG. 1 schematically illustrates a preferred version of the process of this invention.

The alkali concentrate comprises dissolved hydroxides of the cations of the fumarate and LMA salts, e.g., elements of Group I of the Periodic Table, preferably sodium and potassium, and/or ammonia. The alkali concentrate can be recycled back into the biotechnical conversion of fumaric acid into LMA and reused there for neutralizing the fumaric acid. The acid concentrate and the alkali concentrate are generally continuously withdrawn from the EDU as described herein.

In addition to the three cells utilized for the acid cycle, the alkali cycle and the salt/diluted product cycle, the EDU can optionally also contain an anode rinsing cycle and/or a cathode rinsing cycle. The anode rinsing cycle uses an acid solution, preferably a LMA solution. The optionally provided cathode rinsing cycle uses an alkali solution, preferably the same alkali used for neutralization of the fumaric acid before the beginning of the biotechnical conversion.

The process of this invention is particularly economical if the reaction mixture is separated in an EDU containing at least one bipolar membrane. On this membrane, hydrogen and hydroxyl ions are produced by electrodialytic dissociation; these ions can be utilized directly for neutralization of ions having contrary electric charge respectively. During this process, practically no hydrogen gas, and no oxygen gas, are produced.

Unless indicated otherwise herein, all details of the dialysis portion of this invention are fully conventional and readily determinable by routine considerations including apparatus selection and design, membrane selection and relevant parameters, flow rates, cycle configurations, operating conditions, solution compositions, etc. in view of this disclosure; see, for example, Chem.-Ing.-Techn. 56 : 214-220 (1984); and Kirk-Othmer, Encycl. Chem. Technology, 3rd Ed., 8 : 726-738 (1979); and Chem.Eng. June 11: 77-84 (1984); and Spiegler, K.S., Principles of desalination, Academic Press, New York (1966); and Desalination 24 : 129 (1978); and Desalination 47 : 201 (1983); and Membr. Sci. 10 : 81 (1982).

Using this well known technique for working-up solutions of L-malate produced by biotechnical conversion of fumarate results in the following advantages:

As fumaric acid has a rather low solubility in water it is more efficient to use alkali fumarates, especially $NH_4$-fumarate, which results in a high concentration of L-malate and consequently in a favorable working-up process for LMA.

The electrodialysis causes the separation of the alkali (or $NH_4$) ions from the acid residues. The solution containing alkali (or $NH_4$) ions is recycled directly for neutralizing fumaric acid for a new batch.

Nearly no alkali is lost and additionally a high concentration of fumarate is obtained.

It is convenient to run the EDU at the temperature of the broth leaving the bioreactor, e.g., 25°-40° C., preferably 30° C. This temperature is substantially lower than the temperature allowed for the dialysis membranes.

It is important to run the EDU with high throughput of the liquids, especially of the solution from the fermentation broth. The flow between the dialysis membranes has to be turbulent in order to keep the boundary layer as thin as possible and to reduce the polarization of the cell by high concentration in the boundary layer.

As soon as the desired concentrations prevail in the acid and alkali cycles, a partial stream of acid and of alkali is withdrawn continuously from each cycle. The thus-withdrawn amounts of liquid are continuously replaced by water. The discharged quantity of acid and of alkali is as large as the throughput of acid and of alkali through the membranes of the EDU.

For reason of saving steam during the downstream processing of the LMA solution and the recycling of the alkali solution it is advantageous to have a steady state concentration of LMA and alkali in the corresponding solutions which are as high as possible. Attainable are concentrations up to 120 g/l of LMA in the acid solution and 30-40 g/l of alkali (or $NH_4$) in the alkali solution.

To a large extent, the fumaric acid is normally already precipitated in the acid concentrate; the acid can be retained on a filter in the acid cycle and removed from the latter. This fumaric acid is preferably reintroduced into the bioreactor for the biotechnical conversion into LMA.

At the beginning of electrodialysis, the salt/diluted product cycle is charged with the reaction mixture from the biotechnical conversion of fumarate into L-malate, e.g., from the process of U.S. Pat. Nos. 654,070 or 592,977, which disclosures are incorporated by reference herein, or any other.

Typically, these reaction mixtures contain less than 20 g/l, preferably less than 15 g/l of cellular substances at the outlet of the bioreactor. By centrifuging and consecutive filtration using a filter press the cellular material is substantially removed from the fermentation broth.

Typical concentrations in the aqueous solution fed to the EDU after removal of the cellular material from the fermentation broth are 4.5-5% by weight of alkali (or $NH_4$) fumarate and 20-25% by weight of alkali (or $NH_4$) malate.

With progression of electrodialysis, the reaction mixture is depleted of fumarate and L-malate until it contains only residues of these salts and is present as the diluted product. Then the electrodialysis and the diluted product cycle are interrupted, and the entire diluted product is withdrawn. Typical residue amounts of L-malate at this point of interruption are in the range of 1-2 g/l. Optionally, this cycle can be flushed with water. Ammonia or a fungicide/bactericide can be added to the flushing water so that the microorganisms are destroyed which have been retained in the cycle (for example on the membranes).

Subsequently, the salt/diluted product cycle is filled with fresh reaction mixture, and electodialysis is restarted.

In the first concentration step, the acid concentrate is brought to a concentration of LMA of 70-75% by weight, e.g., by evaporation at a temperature of below 60° C., e.g., 30°-55° C. and reduced pressure, e.g., 30-60 mbar. It is then cooled to ambient temperature. The thus-crystallized fumaric acid, containing only a small amount of LMA, e.g., 1-2% by weight, is separated. The remaining NMA solution in the second concentration step is brought to a concentration of LMA of more than 80% by weight, e.g., 80-83% by weight, e.g., by again evaporating at a temperature below 60° C., e.g., 30°-55° C., and 30-60 mbar. It is then cooled to ambient temperature. The thus-crystallized LMA, containing the largest portion of the small amount of remaining fumaric acid, is separated. In case of stricter purity requirements (e.g., fumaric acid contents in the LMA of even lower than 0,1%) this second concentration step can be repeated. The LMA solution remaining after the second concentration step is concentrated stepwise, e.g., at 50°-55° C., —preferably at lower than atmospheric pressure, e.g., 50-60 mbar—until the amount of liquid remaining is merely 7-15%, typically about 10% by weight of the starting quantity for the last concentration step.

The fumaric acid, containing only a small amount of LMA which was crystallized during cooling after the first concentration step can be recycled back into the bioreactor to produce more LMA from biotechnical conversion. The fumaric-acid-containing LMA crystallized upon cooling after the second concentration step can also be recycled, i.e., into the acid concentrate intended for the first concentration step.

The liquid remaining after the third concentration step in a saturated LMA solution and contains practically all of the L-malate and fumarate in dissolved form. This liquid is preferably passed over a strongly acidic cation exchanger to dissociate malate and fumarate. Thereafter the liquid is reintroduced into the acid concentrate.

In cases where the LMA purity requirements are less strict, one or more of the aforedescribed working-up steps can be omitted. In general, the purity of the LMA produced by the process of FIG. 1 of this invention is in the range of 98,5-99.5% by weight (dry basis).

The process of this invention has the following advantages, inter alia:

LMA and fumaric acid are directly separated without precipitation reactions.

Practically no fumaric acid is lost.

The valuable products are obtained in a careful manner.

The reaction mixture can be worked up in the EDU continuously into the desired acid and alkali concentrates.

One of the many reaction mixtures suitable for use in the process of this invention can be prepared as follows, for example. The cellular substance, incubated in a conventional bioreactor under sterile conditions (for example using the fungus *Aspergillus wentii*), is separated from the culture liquor and charged as the inoculum into a vessel of a simple structure containing an (ammonium) fumarate solution. This solution is stirred and a small amount of oxygen necessary to sustain the metabolism of the fungus is added. Biotechnical conversion is finished, e.g., as soon as about 85% by weight of the fumarate is present as L-malate.

The cellular substance is separated from this reaction mixture according to known methods. The reaction mixture—optionally after filtration over active carbon—is separated in the EDU. The acid concentrate is worked up as illustrated schematically in FIG. 1. The alkali concentrate is recycled into the bioreactor; the practically salt-free diluted product is discarded.

The flow chart begins with the reactor 1 for the biotechnical conversion of fumarate into L-malate. The reaction mixture is discharged from the reactor and the cellular substance 3 is separated therefrom by means of the separator 2. The reaction mixture is optionally passed through an active carbon filter 4 and charged into the EDU 5. The cycles through the EDU are not illustrated in FIG. 1. Acid concentrate 6 and alkali concentrate 7 are continuously withdrawn from the EDU. Both concentrates can initially be collected in tanks, not illlustrated, before the alkali concentrate is introduced into the reactor 1 and the acid concentrate is passed on to the working-up operation.

As soon as the salt concentration in the salt/diluted product cycle has dropped to a predetermined value, the diluted product 8 is completely removed from the cycle. This cycle can be flushed with water before charging with a new quantity of reaction mixture.

The acid concentrate 6 is conducted through a separator 9 to separate crystallized fumaric acid. The fumaric acid can be crystallized as early as in the acid concentrate if its saturation concentration is exceeded. Optionally, this separator can also be arranged in the acid cycle. The fumaric acid 10 is recycled—optionally after intermediate storage—into the reactor for biotechnical conversion.

The acid concentrate 11 is concentrated in the first concentration step in the (vacuum) evaporator 12, thus liberating water 13. Additional fumaric acid is separated from the cooled-off acid concentrate 14 in separator 15 and likewise recycled—optionally after intermediate storage—into reactor 1. The acid concentrate 17 is concentrated in the second concentration step in precrystallizer 18 (e.g., an evaporation crystallizer), thus liberating additional water 19. Fumaric-acid-containing LMA 22 is separated in separator 21 from the cooled acid concentrate 20 and recycled upstream to evaporator 12. The concentrated LMA solution 23 is concentrated, for example stepwise, in the evaporation crystallizer and separator 24, down to a remainder 25 of the initially charged liquid.

The crystallized LMA 26 is separated and removed from the installation. The remaining liquid 25 is admixed to the acid concentrate 11 upstream of evaporator 12 after reacting the undissociated malate and fumarate—preferably via a cation exchanger 27.

In case of stricter purity requirements, e.g., as discussed above, the LMA solution 23 can once again be passed through precrystallizer 18 and separator 21, thus removing more water 19 and fumaric-acid-containing LMA 22.

The evaporator for removal of excess water and the installation for recovery of LMA by crystallization are conventional and similar to those discribed in Ullmanns Encyklopädie der technischen Chemie, 4.Auflage, 9 : 624–636 (1975) for recovery of citric acid.

To prevent the LMA from racemization and evaporation and crystallisation are carried out at reduced pressure and a temperature below 60° C.

Figure 2:
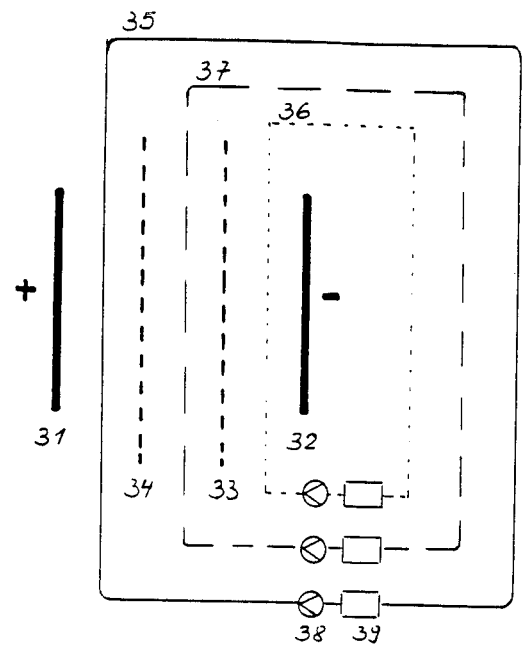
FIGS. 2 and 3 schematically illustrated preferred apparatus and dialysis cycles useful in the process of this invention.

FIG. 2 is a schematic view of the cycles through a three-cell EDU. A cation exchanger membrane 33 and an anion exchanger membrane 34 are arranged between the anode 31 and the cathode 32. The acid cycle 35 passes through the cell lying in front of the anode; the alkali cycle 36 passes through the cell lying in front of the cathode. The salt/diluted product cycle 37 passes through the middle cell bounded, on the anode side, by the anion exchanger membrane and, on the cathode side, by the cation exchanger membrane. The liquids are respectively circulated by means of pumps 38. Each cycle contains a pump receiver 39. The other auxiliary devices and the current supply for the EDU are not illustrated.

Figure 3:
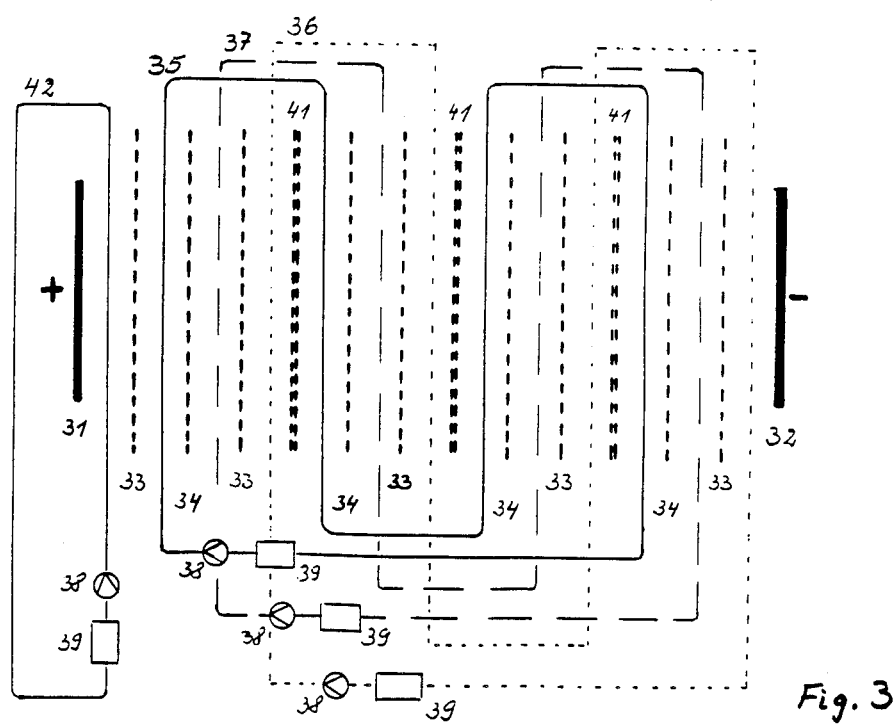

FIG. 3 schematically shows the cycles through an EDU containing three bipolar membranes 41. The cycles are analogous to FIG. 2. This EDU furthermore comprises an anode rinsing cycle 42.

The feed conduits and discharge conduits for the cycles are not included in the illustrations of FIGS. 2 and 3.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE

The EDU consists of three cells and contains an anion exchanger membrane and a cation exchanger membrane, arranged analogously to FIG. 2. The commercially available membranes consists, for example, of crosslinked polystyrene. The cation exchanger membrane contains $SO_3^-$ groups, introduced by sulfonation; the anion exchanger membrane contains quaternary ammonium groups ($NH_4^+$).

Each membrane has an active surface area of 148 $cm^2$. The spacing of the membranes from one another and from the electrode is respectively about 1.4 cm.

Before the beginning of electrodialysis, the cycles contain the following solutions:

salt/diluted product cycle: 350 g of an aqueous solution containing 144.1 g of $NH_4$ malate (about 41.2% by weight) and 16.3 g of $NH_4$ fumarate (about 4.7% by weight), acid cycle: 400 g of a solution of 40 g of LMA in distilled water, alkali cycle: 500 g of drinking water with a small amount of $NH_3$ to increase electrical conductivity.

During electrodialysis, a direct current of about 1.5 A flows through the EDU. The direct voltage is about 10 V at the beginning of electrodialysis, toward the end about 6 V; the voltage is controlled for constant current through the EDU.

The $NH_3$ gas produced at the cathode is washed back. The circulating pumps convey respectively 10 liters per hour. The cells are completely filled with liquid at all times. For this example, liquid was neither removed from the cycles nor introduced into the cycles.

After an operating period of 36 hours, the following results were obtained:

The fumaric acid was present in the acid concentrate mainly in crystallized form. From the acid concentrate, 8.2 g of crystallized product was separated consisting practically entirely of fumaric acid.

The acid concentrate was concentrated for the first time at 50° C. and a pressure of about 50 mbar (absolute) to a content of 73% by weight of LMA and cooled to 23° C. Separation yielded 4.7 g of a crystallized product consisting of 1.2 g of LMA and 3.5 g of fumaric acid.

The remaining acid concentrate was concentrated for the second time at about 50° C. and a pressure of about 50 mbar (absolute) to a content of 83% by weight of LMA and cooled to 23° C. Separation yielded 36.2 g of a moist crystallized product consisting of 35.0 g of LMA and 0.5 g of fumaric acid.

The remaining acid concentrate was concentrated stepwise at about 50° C. and a pressure of about 40 mbar (absolute) down to a residual quantity of liquid, thus obtaining 108.3 g of crystallized product and 11.6 g of liquid.

The crystallized product was dried to a water content of below 1%.

The process described herein can also be performed continuously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing L-malic acid by separation from a reaction mixture produced in the biotechnical conversion of fumaric acid salts to L-malic acid salts, which mixture is substantially free of cellular substances comprising electrodialysing the reaction mixture in an electrodialysis unit having at least three cells separated from one another by dialysis membranes thereby continuously separating out three solutions, which are an acid concentrate solution containing L-malic acid and fumaric acid, an alkali concentrate solution containing the hydroxide of the cation of the fumaric acid and L-malic acid salts, and a diluted product solution containing nonionic components of the reaction mixture and residual fumarate and L-malate; and recovering purified L-malic acid by concentration/crystallization of the acid concentrate 2. A process of claim 1 wherein the electrodialysis unit comprises at least one bipolar membrane which serves as the predominant source of the hydrogen and hydroxyl ions required for neutralization of the acidic and alkaline species produced during the dialysis.

3. A process of claim 1 wherein the electrodialysis unit comprises a flushing cycle.

4. A process of claim 1 wherein the reaction mixture produced in said biotechnical conversion is essentially free from cellular substances prior to use in the electrodialysis step.

5. A process of claim 1 wherein said biotechnical conversion comprises a step of neutralizing fumaric acid with a base to form a fumarate, and the process further comprises recycling said alkali concentrate solution into the biotechnical conversion to provide said base.

6. A process of claim 5 wherein the acid concentrate emanating from the electrodialysis step contains crystallized fumaric acid, and further comprising separating the latter crystallized fumaric acid and recycling it into the biotechnical conversion as a source of fumaric acid.

7. A process of claim 1, wherein the acid concentrate emanating from the electrodialysis step contains crystallized fumaric acid.

8. A process of claim 7, further comprising separating the latter crystallized fumaric acid and recycling it into the biotechnical conversion as a source of fumaric acid.

9. A process of claim 1 further comprising the following concentration/crystallization steps for the acid concentrate:

in a first concentration step, concentrating the acid concentrate at a temperature below 60° C. to achieve a concentration of L-malic acid therein of 70–75% by weight, separating the crystallized fumaric acid, which contains only a small amount of L-malic acid, from the resultant L-malic acid solution, in a second concentration step, concentrating the resultant L-malic acid solution at a temperature below 60° C. to achieve a concentration of L-malic acid therein of more than 80% by weight, cooling the solution to ambient temperature, and separating the crystallized L-malic acid, which contains a residual amount of fumaric acid, from the remaining L-malic acid solution.

evaporating the L-malic acid solution remaining after said second concentration step to about 10% of its weight at the end of the second concentration step, and separating the resultant crystallized purified L-malic acid.

10. A process of claim 9, further comprising recycling the fumaric-acid-containing L-malic acid, crystallized-out in the coolign step after the second concentration step, back into the acid concentrate solution fed into the first concentration step.

11. A process of claim 9 wherein said step of evaporating the L-malic acid solution remaining after said second concentration step is carried out under less than atmospheric pressure.

12. A process of claim 9 wherein said first and second concentration steps are carried out under less than atmospheric pressure.

13. A process of claim 9 which is performed continuously.

14. A process of claim 9 wherein the L-malic acid solution remaining after said second concentration step, prior to said evaporating step, is again concentrated at a temperature below 60° C. to achieve a concentration of L-malic acid therein of more than 80% by weight and is then cooled to ambient temperature; and wherein the resultant L-malic acid which crystallizes-out is separated, and the resultant L-malic acid solution remaining is then subjected to said evaporating step.

15. A process of claim 9, further comprising the steps of biotechnically converting fumaric acid salts to L-malic acid salts, and recycling the fumaric acid crystallized-out after said first concentration step back into the biotechnical conversion as a source of fumaric acid.

16. A process of cl aim 15, further comprising recycling the fumaric-acid-containing L-malic acid, crystallized-out in the cooling step after the second concentration step, back into the acid concentrate solution fed into the first concentration step.

17. A process of claim 16 which is performed continuously.

* * * * *

UNITED STATES PATENT AND TRADEMARK OFFICE
CERTIFICATE OF CORRECTION

PATENT NO. : 4,874,700

DATED : October 17, 1989

INVENTOR(S) : REINHOLD SEIPENBUSCH

It is certified that error appears in the above-identified patent and that said Letters Patent is hereby corrected as shown below:

Column 8, claim 9, line 48:

before "separating" the following should be inserted:

--cooling the concentrate to ambient temperature, and--

Signed and Sealed this

Thirtieth Day of October, 1990

Attest:

HARRY F. MANBECK, JR.

Attesting Officer

Commissioner of Patents and Trademarks